US010895453B2

(12) United States Patent
Stemkens et al.

(10) Patent No.: US 10,895,453 B2
(45) Date of Patent: Jan. 19, 2021

(54) PROCESS FOR THE DETERMINATION OF THE CROSS-SECTIONAL AREA AND VOLUME OF AN OBJECT

(71) Applicant: PERACUTUS HOLDING B.V., Roggel (NL)

(72) Inventors: Hans Stemkens, Roggel (NL); Frans Houwen, Roggel (NL)

(73) Assignee: PERACUTUS HOLDING B.V., Roggel (NL)

( * ) Notice: Subject to any disclaimer, the term of this patent is extended or adjusted under 35 U.S.C. 154(b) by 764 days.

(21) Appl. No.: 15/302,757

(22) PCT Filed: Apr. 10, 2015

(86) PCT No.: PCT/EP2015/057838
§ 371 (c)(1),
(2) Date: Oct. 7, 2016

(87) PCT Pub. No.: WO2015/155331
PCT Pub. Date: Oct. 15, 2015

(65) Prior Publication Data
US 2017/0038200 A1    Feb. 9, 2017

(30) Foreign Application Priority Data

Apr. 10, 2014 (EP) ..................... 14164274

(51) Int. Cl.
*G01B 13/00*        (2006.01)
*A61B 5/107*        (2006.01)
(Continued)

(52) U.S. Cl.
CPC ............ *G01B 13/00* (2013.01); *A61B 5/1072* (2013.01); *A61B 5/1073* (2013.01); *G01B 13/20* (2013.01); *G01F 17/00* (2013.01); *G01F 23/00* (2013.01)

(58) Field of Classification Search
CPC .... A61B 5/1072; A61B 5/1073; G01B 13/00; G01B 13/20; G01F 17/00; G01F 23/00
See application file for complete search history.

(56) References Cited

U.S. PATENT DOCUMENTS 3,570,474 A    3/1971  Jonson
4,122,837 A   10/1978  Leonard
(Continued)

FOREIGN PATENT DOCUMENTS

CA    2375249 A1   12/2000
DE    1019834      11/1957
(Continued)

OTHER PUBLICATIONS

E. Kuhnke, Volumbestimmung aus Umfangmessungen, Folia Angiologica, 1976, pp. 228-232, vol. 24, publisher unknown and city and country unknown.

*Primary Examiner* — Rene T Towa
(74) *Attorney, Agent, or Firm* — Hudak, Shunk & Farine Co. LPA

(57) ABSTRACT

A process for the determination of the cross-sectional area and volume of an object including the steps of a. Providing a container having a closed bottom, an open top, a side wall, a tap at a reference height, b. Providing a flowable medium having a surface in the container, c. Providing at least one measuring means for measuring a height of the surface of the flowable medium in the container relative to the reference height, d. Providing an object having a vertical Z-axis relative to the X,Y plane of the surface and positioning the object in the container, the object being at least partly submerged in the flowable medium, e. Providing calculating means for calculating the cross-sectional area and/or volume of the object in the X,Y plane relative to a position on the Z-axis, f. Opening the tap in the container to allow the flowable medium to flow out of the container, g. Measuring (Continued)

the height of the surface of the flowable medium relative to the reference height as a function of time (h(t)) during the outflow of the flowable medium, h. Calculating the cross-sectional area of the object ($A_o$) as a function of the height relative to the reference height based on the determined height of the surface as a function of time (h(t)) during the outflow of the flowable medium in step f). A device for measuring the cross-sectional area and volume of an object.

12 Claims, 6 Drawing Sheets

(51) Int. Cl.
  *G01F 17/00* (2006.01)
  *G01B 13/20* (2006.01)
  *G01F 23/00* (2006.01)

(56) References Cited

U.S. PATENT DOCUMENTS

| | | | | |
|---|---|---|---|---|
| 4,144,749 | A * | 3/1979 | Whitmore | G01F 17/00 73/149 |
| 4,383,533 | A | 5/1983 | Bhagat et al. | |
| 4,887,231 | A | 12/1989 | Ratliff et al. | |
| 5,063,910 | A * | 11/1991 | Cartier | A61H 9/0078 601/159 |
| 5,450,750 | A * | 9/1995 | Abler | A61B 5/103 73/149 |
| 5,588,428 | A | 12/1996 | Smith et al. | |
| 5,915,386 | A * | 6/1999 | Lloyd | A61B 5/1077 128/897 |
| 6,077,222 | A * | 6/2000 | Lloyd | A61B 5/1073 600/300 |
| 7,147,609 | B2 * | 12/2006 | Turner | A61B 5/107 600/587 |
| 2004/0001204 | A1 | 1/2004 | Boone et al. | |
| 2008/0307874 | A1 | 12/2008 | Healey | |
| 2011/0015512 | A1 * | 1/2011 | Pan | A61B 3/16 600/399 |

FOREIGN PATENT DOCUMENTS

| | | | |
|---|---|---|---|
| DE | 1076323 B * | 2/1960 | ........... A61B 5/1073 |
| DE | 3516361 A1 | 11/1986 | |
| DE | 3535270 A1 | 4/1987 | |
| DE | 4032152 A1 | 4/1992 | |
| FR | 1426229 | 11/1964 | |
| FR | 2774276 A1 | 8/1999 | |
| FR | 2836556 A1 | 8/2001 | |
| GB | 2205163 A | 11/1988 | |
| GB | 2382072 A | 5/2003 | |
| JP | 2012-61083 A | 3/2012 | |
| NL | 8801941 | 3/1990 | |
| WO | 0079255 A1 | 12/2000 | |
| WO | 0175404 A1 | 10/2001 | |
| WO | 2009125327 A1 | 10/2009 | |

* cited by examiner

PROCESS FOR THE DETERMINATION OF THE CROSS-SECTIONAL AREA AND VOLUME OF AN OBJECT

FIELD OF THE INVENTION

The present invention relates to a process to determine the cross-sectional area and volume of an object, a device to perform the measurement, and the use of the device. The invention may be applied in the field of medicine as well as for industrial applications for measuring the cross-sectional area and volume of objects.

BACKGROUND OF THE INVENTION

Lymphedema is swelling of a body part due to accumulation of interstitial fluid. The primary increase in volume is often followed by changes like fibrosis or the development of connective tissue. The prevalence of chronic lymphedema is difficult to determine as different definitions prevail. Still, in the Netherlands 350,000 patients are known (2.2%). In Europe and North America the estimated number of patients having edema is more than 27 million, whereas worldwide over 200 million patients suffer from this disease.

An early and accurate diagnosis is of great importance because effective treatments are possible in many cases. The result of a treatment is determined by measuring local cross-sectional areas and the volume of a leg or an arm.

A great number of different techniques is used to measure edema. These techniques are based on physical or physiological characteristics of edema or skin, or measure circumference and/or (calculate) volume of extremities or body. These include optical techniques (FR2774276, U.S. Pat. No. 5,588,428, DE3535270), ultrasonic techniques (FR2836556), laser absorption (US2004001204), bioelectrical impedance (CA2375249, WO0079255), stretch sensors (DE4032152, WO2009125327, US20080307874), surface deformation sensors (U.S. Pat. No. 4,122,837), gas pressure devices (US20040001204), acoustic techniques (U.S. Pat. No. 4,383,533), immersion in water (WO0175404, NL8801941, DE3516361, FR1426229).

The classical way to measure a leg or arm is by means of a tailor tape. The circumference of the extremity is measured on several places and the volume is subsequently calculated using arithmetic models according to Kuhnke (Folia Angiologica (1976) 24, 228-232). Besides its discontinuous nature, a disadvantage of using the tailor tape is the variation of the force used during the measurement carried out by different persons, influencing the length of the tailor tape and the circumference of the extremity. Also, choosing a reference point is difficult resulting in difficult comparison of results obtained at different times. Finally, the hand and foot are not included and the method is time consuming.

A way to measure the volume of an extremity is the use of the perometer. A leg or arm is placed on a support and a measuring frame moves forth and fro. Data are collected using either of different physical techniques and the information is converted into a 3-dimensional image. Although the technique is quick, it is difficult to reproduce, hand and foot are not included and the device is expensive. Currently, the best method to measure cross-sectional areas and volumes is the total body scan. A patient stands on a platform and is scanned optically in a very short time. The method, however, is very expensive.

A further technique is available by way of immersion of an extremity in water. Immerse extremities in a reservoir containing water and measuring the change in the height of the water goes back as far as the observations of Archimedes. The amount of water displaced is a measure for the volume of the extremity or object.

Water displacement is measured by collecting the water in a second tank using an overflow system or by measuring the increase of the height of the water in the same container in which the extremity is submerged. This so called water tank method is used to measure the volume of whole extremities, including deviant shapes. The method is sensitive to the speed by which the extremity is submerged into the tank and to the position of the extremity in the tank.

A method that is directly correlated to the water tank method is the inverse water volumetry method (WO00175404). Here, the shortness of water is measured. By using a weighing device the entire measuring device is used as one entity. Prior to use, calibration to zero is performed by filling the water tank till the reference point where the water flows in the overflow tube. Afterwards the system is emptied and ready for use. A patient's arm is placed into the device and the tank is filled up to the overflow tube with water. When the whole system is at equilibrium, the patient's arm is removed and the system is disconnected. Subsequently, the display of the weighing device shows the shortness of water compared to the initial situation. This shortness of water represents the volume of the arm. The major diagnostic disadvantage of both the water tank method and the inverse water volumetry method is that the result does not tell which part of the extremity is edemic, i.e. the place(s) where changes in cross-sectional areas have occurred.

FR1426229 discloses a method using water displacement to measure changes in volume of a segment of an extremity as function of time. However, said segment always is a substantial part of the extremity, giving no information of local changes. Another detection method (DE3516361) is based on the displacement of electrical field lines in an electrolyte solution after submerging an extremity. In U.S. Pat. No. 3,570,474 an apparatus for determining body volume changes is disclosed which utilizes a rigid tubular member of surrounding a portion of a body extremity leaving an annular chamber there around. The chamber is in communication with a flow meter which is sensitive to fluid flow into or out of the tube chamber, caused by small and rapid volume changes in the body extremity enclosed within the tube. Use of an annular chamber has also been described in combination with electrodes as detection devices (GB2205163).

There is a need for an accurate, fast and effective technique to detect the onset of edema, assess its severity and monitor its response to treatment.

SUMMARY OF THE INVENTION

The invention relates to a process for the determination of the cross-sectional area ($A_o$) as a function of a height of an object comprising the steps of
a. Providing a container (2) having a closed bottom (5), an open top (3), a side wall (4), a tap (8) at a reference height,
b. Providing a flowable medium (12) having a surface (13) in the container (2),
c. Providing at least one measuring means (7, 9, 10, 11) for measuring a height of the surface (13) of the flowable medium (12) in the container (2) relative to the reference height,
d. Providing an object having a vertical Z-axis relative to the X,Y plane of the surface (13) and positioning the object in the container, the object being at least partly submerged in the flowable medium (12), e. Providing calculating means for calculating the cross-sectional area and/or volume of the object in the X,Y plane relative to a position on the Z-axis, f. Opening the tap (8) in the container (2) to allow the flowable medium (12) to flow out of the container (2), g. Measuring the height of the surface (13) of the flowable medium (12) relative to the reference height as a function of time (h(t)) during the outflow of the flowable medium (12), h. Calculating the cross-sectional area of the object ($A_o$) as a function of the height relative to the reference height based on the determined height of the surface (13) as a function of time (h(t)) during the outflow of the flowable medium in step f).

The process of the present invention provides determination of the cross-sectional area and/or volume of an object, preferably an arm or a leg, in a non-invasive manner and is virtually free of inaccuracies arising from body temperature changes and timing errors.

The process is simple to operate and provides a reproducible result. The calculations necessary for the determination of cross-sectional area and the volume are automatically performed by, for example, a microprocessor and therefore the values for the cross-sectional area and the volume are immediately digitally available.

Another advantage is that the measurement can be performed in less than 5 minutes.

The process is based on common anatomical reference points to guide the clinician performing the measurements. This has the advantage that for example arms of adults and children can be reproducibly measured as well as very thick or very thin legs.

Step a and b

The invention relates to a process for the determination of the cross-sectional area and/or the volume of an object comprising step a and b). According to step a) a container 2 is provided having a closed bottom 5, an open top 3, a side wall 4 and a tap 8. The container 2 may be of any shape. Examples of preferred shapes are cylindrical, elliptical, right-angled and square. It is important that the shape is such that there is no area in the container 2 where flowable medium 12 can be detained. More preferably, the shape of the container 2 is cylindrical.

The container 2 is provided with at least one tap 8. In one embodiment the tap 8 is placed in the bottom 5 of the container 2. In another embodiment the tap 8 is placed at a certain height above the bottom 5 of the container 2. For example the tap 8 can be placed above the bottom 5 at a distance between 1 and 20% of the height of the side wall 4 of the container 2. The tap 8 defines a reference height. Opening of the tap 8 allows a flowable medium 12 to flow out of the container 2. The container 2 may be provided with more than one tap 8 in order to be able to modify or regulate the flow rate of the flowable medium 12 out of the container 2. The taps 8 may be of different diameter and/or type and may be at different heights relative to the bottom 5 of the container 2.

In another embodiment the container 2 can be emptied by removing flowable medium 12 via the open top 3 of the container 2. The flowable medium 12 can be removed via the open top 3 of the container 2, for example by using a hose or a pump.

According to step b) of the process the flowable medium 12 is provided in the container 2.

The flowable medium 12 can be a liquid, a suspension, a colloidal solution, a gel, or a solid. In case a solid is used this is preferably a granular solid. The granular solid or another flowable medium 12 may be easy to clean and disinfect, in order to improve hygienic circumstances. The flowable medium 12 may comprise small beads transmitting an electromagnetic or acoustic signal which is received by an appropriate device.

Preferably, the flowable medium 12 is a liquid, more preferably water.

In one embodiment of the invention, the flowable medium 12 is collected in a second container and the amount of the flowable medium 12 versus time is determined in the second container, using any measuring means, like for example a scale, a flow meter, a pressure meter and a height meter. The second container can be separately provided or the second container can be connected to the first container 2 with a hose or a pipe. Preferably, the hose or pipe comprises a tap or another means for regulation of the flow of the flowable medium 12.

Step c

According to step c the container 2 is provided with at least one measuring means 7, 9, 10 or 11 for measuring the height of the surface of the flowable medium 12 in the container 2.

For example the measuring means 7, 9, 10 or 11 can determine the height of the surface 13 of the flowable medium 12 in the container 2. Alternatively the measuring means 7, 9, 10 or 11 can determine the amount of flowable medium 12 flowing out of the container 2 during a measurement of the cross sectional area and/or volume of the object. The height of the flowable medium 12 can be measured continuously. Here and hereafter, the height of the flowable medium 12 is the vertical distance which is determined between the surface 13 of flowable medium 12 and a chosen reference point on the Z-axis (for example the reference height). The height of the surface of the flowable medium 12 in the container 2 is equal to the position on the Z-axis of the flowable medium 12 in the container 2. Here and hereinafter the phrase 'height of the surface of the flowable medium' can be replaced by the phrase 'position on the Z-axis of the surface of the flowable medium'.

Examples of measuring means 7, 9, 10 or 11 are a pressure sensor, a conduction sensor, a balance, a weighing scale, an altimeter, a tape measure or optical means; preferably the measuring means is a pressure sensor 9. At least one means 7, 9, 10 or 11 for measuring the height is present inside or outside the container 2. The means 7, 9, 10 or 11 for measuring the height can be placed outside or inside the container and do not need to be physically connected with the container. More than one means 7, 9, 10 or 11 for measuring the height of the flowable medium 12 can be present inside or outside the container 2, whereby these means may be of different types or using different measuring principles. These means 7, 9, 10 or 11 may be at different heights relative to the bottom 5 of the container 2. Measuring accuracy can be improved by combining the measuring results obtained simultaneously by more than one measuring means, using statistical tools. The measuring means provide an output which is used as input for the calculating means.

Step d

According to step d) an object having a vertical Z-axis relative to the X,Y plane of the surface 13 is provided which is at least partly submerged in the flowable medium 12. The Z-axis is perpendicular to the horizontal surface 13 of the flowable medium 12 (which is defined by the X,Y plane). The object can be an object of any shape. The cross-sectional area of the object perpendicular to the Z-axis to be measured in the container 2 is smaller than the cross-sectional area of the container 2 perpendicular to the Z-axis. The object preferably is a part of a human body, more preferably an arm or a leg.

The cross-sectional area of the object is determined in the X, Y plane of the surface 13 as function of the height relative to the Z-axis. The cross-sectional area of the object is determined at the interface between air and the surface 13 of the flowable medium 12.

Step e

According to step e) of the process calculating means are provided for calculating the cross-sectional area and/or volume of the object in the X,Y plane relative to a position on the Z-axis. The calculating means use the output of the measuring means to calculate the cross sectional area and/or the volume of (parts) of the object. The object can be a (segment) of an extremity of a human body. The calculating means are preferably digital means. In this way the results of the calculation are also digital and can be stored and shared in an easy way. For example, the calculating means contains a microprocessor.

Step f

According to step f) the tap 8 in the container 2 is opened to allow flowable medium 12 to flow out of the container 2. With the size and type of the tap 8 and the position of the tap 8 relative to the height of the surface 13 of the flowable medium 12, the flow rate of the flowable medium 12 can be influenced. For example by opening the tap 8 partly or by opening more than one tap simultaneously, the flow rate of the flowable medium 12 can be changed. By influencing the flow rate the measurement can be adjusted to measure differently sized objects, thereby optimizing measurement time and accuracy of the measurement. For example, when a large object is placed in the container 2 the tap 8 can be opened just a little bit to ensure that the flowable medium 12 is not flowing too fast and the measurement is not inaccurate. For example when an object with a small cross-sectional area is present in the container 2 it might be necessary to open two taps simultaneously to make sure that the measurement time is not too long.

It is possible to adjust the flow rate of the flowable medium 12 during the measurement, as long as the exact flow at any time is determined during the measurement.

Step g and h

According to step g) of the process the change of the height of the surface (13) of the flowable medium 12 relative to the reference height is measured as a function of the time. According to step h) of the process the cross-sectional area ($A_o$) of the object is calculated as a function of the height relative to the reference height as a function of time (h(t)) during the outflow of the flowable medium in step f).

The volume of any defined segment of the object can be calculated based on to the height of the object relative to the reference height. Further, it is possible to correct the cross-sectional area ($A_o$) of the object as a function of height for an offset of the object relative to the reference height in a vertical direction of the object.

Measurement of the cross-sectional area and volume of the object is based on a mathematical description of a deflating container. The container 2 is filled with flowable medium 12 till a height H. At a certain moment, t=0, the tap 8 is opened and the flowable medium 12 flows out of the container.

The rate of deflation of the flowable medium 12 in the container 2 is linked to the height of the flowable medium in the container 2 at any moment. Mathematically, the rate of deflation, can be described using the non-stationary mass balance equation and the Bernoulli equation.

Mathematical Deduction

In the following part the mathematical deduction of the theory behind the measurement is described. The symbols used in the mathematical deduction have the following meaning:

$A_c$=cross-sectional area of the container $A_{cs}$=cross-sectional area of the annular space between the object and the wall of the container at height h $A_o(h)$=cross-sectional area of the object at height h $C_c$=factor correcting for contraction side effects $C_f$=factor correcting for friction side effects $\frac{dh}{dt}$ = differential quotient, change in height of the flowable medium in the container as function of time $\frac{\Delta h}{\Delta t}$ = difference quotient, change in height of the flowable medium in the container as function of time $\frac{dm}{dt}$ = change in mass as function of time dt=change in time $\frac{dV}{dt}$ = change in volume as function of time g=acceleration due to gravity h=height of the flowable medium in the container relative to the reference height h(t)=height of the flowable medium as function of time P(h)=pressure as function of height $Q_{v,in}$=flow in $Q_{v,out}$=flow out r=radius of the tap opening R=radius of a cylindrical container t=time ρ=relative density v=rate A non-stationary mass balance of a deflating container is set up as follows:

$$\frac{dm}{dt} = Q_{v,in} * \rho - Q_{v,out} * \rho + \text{production} \quad (1)$$

As no flowable medium is added to the container and no flowable medium is produced from the start of the measurement, t=0, the non-stationary mass balance equation can be written as follows:

$$\frac{dm}{dt} = -Q_{v,out} * \rho \qquad (2)$$

In a deflating container—$Q_{v,out}$ is a function of the height of the flowable medium and therefore:

$$\frac{dm}{dt} = -Q_{v,out}(h) * \rho \qquad (3)$$

Expressing $$\frac{dm}{dt} \text{ as } \rho * \frac{dV}{dt}$$

becomes:

$$\rho * \frac{dV}{dt} = -Q_{v,out}(h) * \rho \qquad (4)$$

Or $$A_{cs} * \frac{dh}{dt} = -Q_{v,out}(h) \qquad (5)$$

The Bernoulli equation describes the relation between the potential energy of a flowable medium and the rate at which the flowable medium leaves a container via a tap.

$$\rho g h + P(h) + 1/2\rho\left(\frac{dh}{dt}\right)^2 = \rho g h_{out} + P_{out} + 1/2\rho(v_{out})^2 \qquad (6)$$

As $$\frac{dh}{dt} \ll v_{out},$$

$P(h)=P_{out}$ and $h_{out}=0$ equation (6) becomes:

$$v_{out} = \sqrt{2 \cdot g \cdot h} \qquad (7)$$

Substitution of (7) in (5) renders:

$$A_{cs} * \frac{dh}{dt} = -\pi r^2 \cdot \sqrt{2 \cdot g \cdot h} \qquad (8)$$

Further, a contraction factor and a friction factor are included to correct for side effects during flowing out of the flowable medium:

$$A_{cs} * \frac{dh}{dt} = -c_c c_f \cdot \pi r^2 \cdot \sqrt{2 \cdot g \cdot h} \qquad (9)$$

If an object to be measured is present in the container, $A_{cs}$ is unknown during deflation of the container, and an analytical solution of the differential equation (9) is not possible.

Replacing the differential quotient $$\frac{dh}{dt}$$

by the difference quotient $$\frac{\Delta h}{\Delta t}$$

renders:

$$A_{cs} * \frac{\Delta h}{\Delta t} = -c_c c_f \cdot \pi r^2 \cdot \sqrt{2 \cdot g \cdot h} \qquad (10)$$

which approximates the differential equation (9).

Because $A_{cs}=A_c-A_o$ and $A_c$ is known at any height, $A_o$ can be calculated from equation (10) at any height.

Measuring an Object

The presence of an object in the container has no influence at all on the rate at which a flowable medium flows out of the container: $v_{out}$ is only a function of h(t).

The object will occupy part of the cross-sectional area of the container at any height h. Because of the presence of the object the height of the flowable medium between the object and the wall of the container (the annular space) will descent faster. In other words, the change in height versus time $$\left(\frac{\Delta h}{\Delta t}\right),$$

will be greater at any moment if an object is present in the container. Thus, the rate of descent of the height of the flowable medium in the annular space is a direct function of the local cross-sectional area of the object, if the height-time profile of the reference container without the object is known.

In order to measure an object, the object is placed in the container and the container is filled with a flowable medium. At t=0 the tap 8 is opened and the flowable medium is allowed to flow out of the container. The measurement consists of determining the height h of the flowable medium versus time t. By using very short time intervals a high resolution is achieved and the discrete set of measuring points nearly becomes continuous.

The cross-sectional area of the object at any height is then calculated by comparing $$\left(\frac{\Delta h}{\Delta t}\right)$$

of the flowable medium in the container in presence of the object with the reference $$\left(\frac{\Delta h}{\Delta t}\right)$$

determined when no object is present in the container.

Strictly speaking, there is no volume of the object at a certain height h. A volume element, $A_o*\Delta h$, does exist though between the two heights h and h+Δh. By mathematically adding up the volume elements $A_o*\Delta h$ the actual volume of any finite segment between two chosen boundaries can be calculated.

The difference quotient $$\left(\frac{\Delta h}{\Delta t}\right)$$

used here, is comparable to the classical approach (e.g. by Kuhnke) in which volumes are calculated based on circumferences, measured discontinuously with a tailor tape. However, as the steps $$\left(\frac{\Delta h}{\Delta t}\right)$$

are very small a nearly continuous measurement is achieved.

The result of the measurement is dependent on the temperature of the flowable medium. Therefore, the temperature of the flowable medium should be measured and the results should be corrected for the relative density, ρ, of the flowable medium used. Of course, in case the temperature of the flowable medium in the reference container is equal to the temperature during the measurement in the presence of the object, no correction is needed.

In another embodiment of the invention, a container is filled up with a flowable medium during the measurement instead of applying a deflating container. The mathematical description of such measurement would be equivalent as described above. In equation (1)—$Q_{v,out}$ would be replaced by $Q_{v,in}$. The flowable medium may be added from the bottom of the container, or from the top, or from any height in between. The rate of adding flowable medium is allowed to change during the measurement, as long as the exact flow at any time is known.

In a further embodiment of the invention the lower part of the container is divided into two compartments by placing a partitioning. In such cases each compartment preferably contains a tap and measuring means, while both measuring means are connected to the calculation means to independently measure the cross-sectional area or volume of each subject in each compartment. This enables the measurement of e.g. a body (chest and hips) of a person followed by a separate measurement of both legs simultaneously. The same embodiment can also be applied to measure two arms simultaneously. Instead of dividing a container in compartments, two separate containers may be used simultaneously. The invention is also directed to a device for performing the process for the determination of the cross-sectional area and volume of an object, wherein the device comprises a container comprising a closed bottom, an open top, at least one tap and at least one means for measuring the height of a flowable medium in the container. The container may be of any shape. Examples of preferred shapes are cylindrical, elliptical, right-angled and square. More preferably, the shape of the container is cylindrical. Preferably, the at least one means for measuring the height (7, 9, 10, 11) is selected from a pressure sensor, a conduction sensor, a balance, a weighing scale, an altimeter, a tape measure and optical means.

When the container is in use for the measurement, the container also comprises a flowable medium and an object. Preferably, the object is an arm or a leg.

The invention is further directed to the use of the process for the determination of the cross-sectional area and volume of an object for assessing tissue edema. Preferably, the tissue edema in an arm or a leg is assessed.

BRIEF DESCRIPTION OF THE DRAWINGS

The present invention is further elucidated referring to FIGS. 1, 2, 3, 4A, 4B, 5A, 5B, 6, 7 and 8 in which.

DETAILED DESCRIPTION OF THE INVENTION

Figure 1:
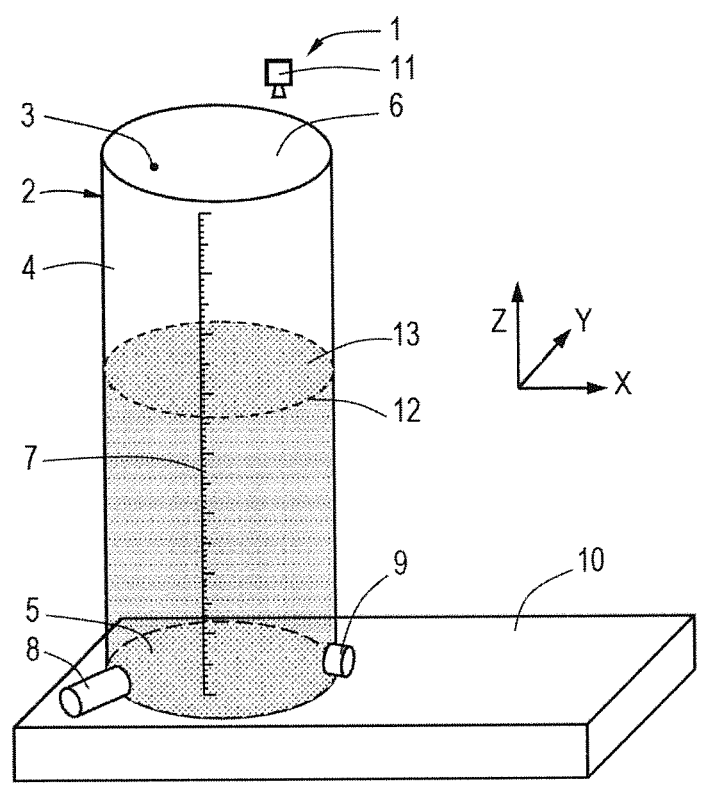
FIG. 1 illustrates the device for the determination of the cross-sectional area and/or the volume of an object.

In FIG. 1 the device 1 for the determination of the cross-sectional area and/or the volume of an object is shown. The device comprises a cylindrical container 2. The container has an open top 3, a side wall 4 and a closed bottom 5. On the container a scale 7 can be provided so that the (change of the) height of flowable medium 12 in the container 2 can be read. The container is provided with an outlet preferably comprising a tap 8. The container 2 has a volume 6, which is larger than the total volume of the body part which will be inserted in the container 2 and the volume of flowable medium 12. The flowable medium 12 has a surface 13 which defines the X,Y-plane.

The cylindrical container 2 can be provided with a pressure sensor 9. Above the container 2 an altitude sensor 11 can be provided that can determine the height of the surface 13 of the flowable medium 12. The container 2 can also been placed on a weighing scale 10.

The device 1 optionally contains one or more taps and/or measuring means.

Figure 2:
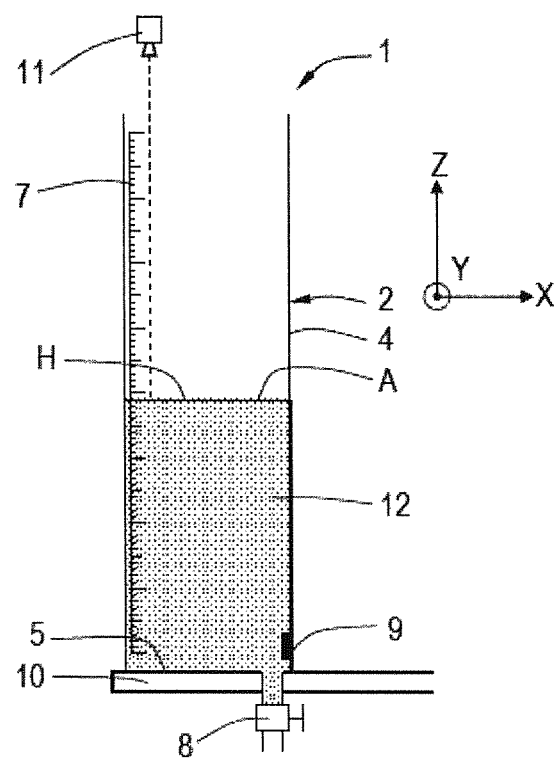
FIG. 2 illustrates a side view of a container comprising a flowable medium.

FIG. 2 shows a side view of the device 1, comprising the container 2 having side wall 4, bottom 5 and opening 3 with tap 8. The container 2 is provided with a scale 7, a pressure sensor 9, a weighing scale 10 and an altitude sensor 11. The X-axis and the Y-axis lie in the plane of the surface 13 of the flowable medium 12. The Z-axis is perpendicular to the X and Y axis. The container (2) is filled to a level H with flowable medium 12. The cross sectional area of the flowable medium 12 is defined by A.

Figure 3:
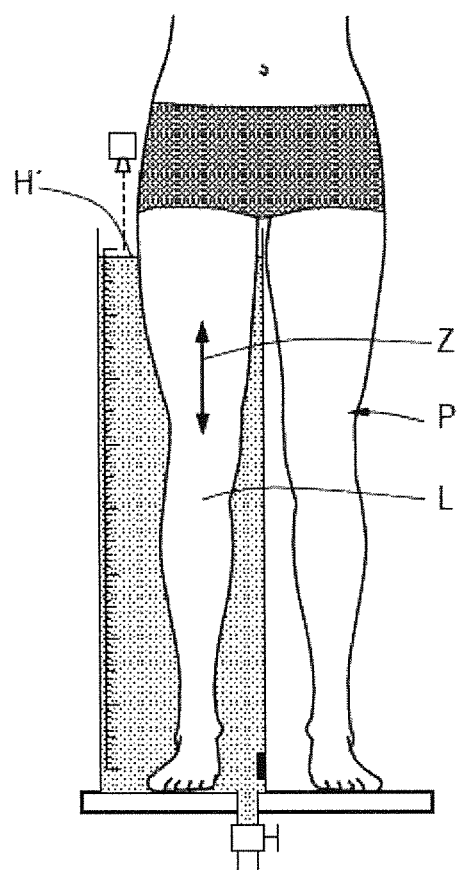
FIG. 3 illustrates a side view of a container comprising a flowable medium and a leg of a person.

FIG. 3 shows a side view of a container 2 according to FIG. 2. A person P is standing with one leg L in the container. The container is filled with flowable medium 12 in the container 2 to level H'. The Z-axis is illustrated by the arrow Z on the leg L of the person P.

Figures 4A, 4B:
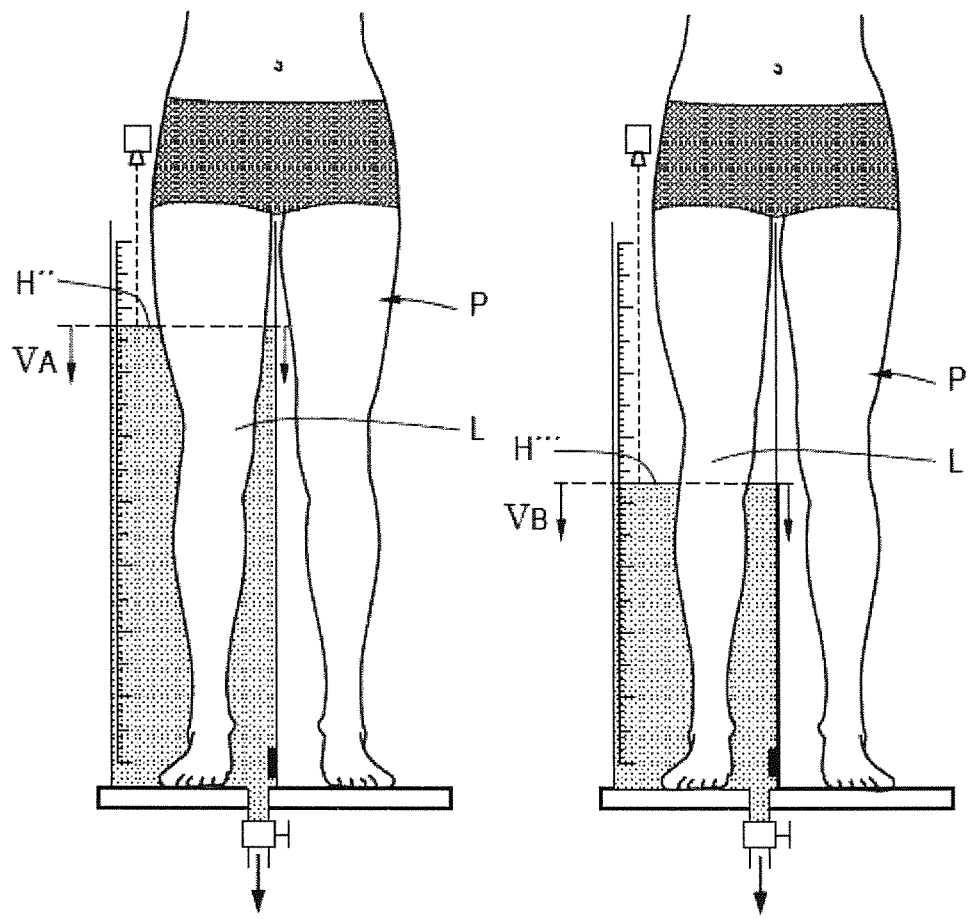
FIGS. 4A and 4B illustrate a side view of a container comprising a flowable medium and a leg of a person at different stages of the measurement.

FIGS. 4A and 4B illustrate a side view of a container 2 according to FIG. 3. The container 2 comprises a flowable medium 12 and a leg L of a person P. During the measurement flowable medium 12 is removed via the tap 8. FIGS. 4A and 4B show the container 2 at different stages of the measurement. According to FIG. 4A the height of the flowable medium 12 is lowered to height H" and according to FIG. 4B the height of the flowable medium 12 is further lowered to height H'''.

Figure 5A:
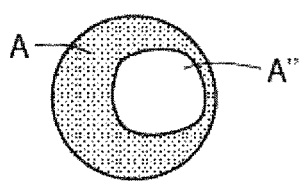
FIGS. 5A and 5B illustrate the cross-section of the container and body at a height H" and H'" (see FIGS. 4A and 4B).
Figure 5B:
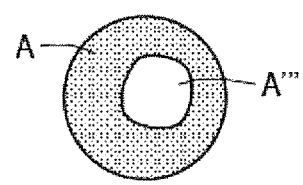
Figure 6:
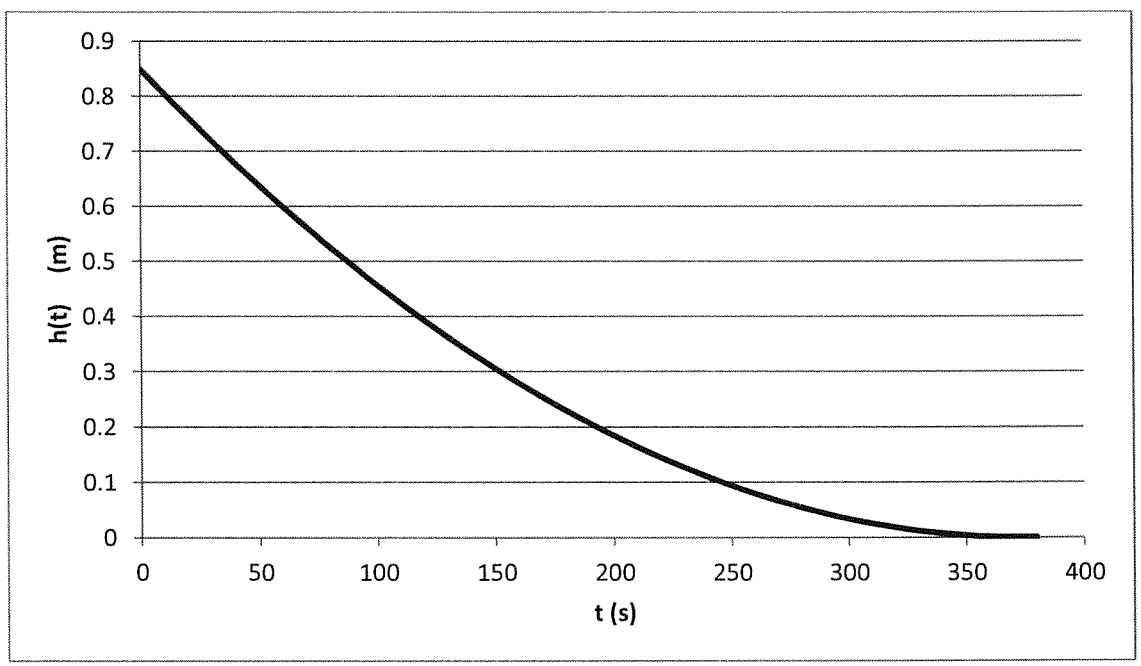
FIG. 6 illustrates the height of a water column in a deflating cylindrical container as function of time. The following assumptions are made: R=0.15 m, r=0.005 m, $C_c$=0.62 and $C_f$=0.73.

FIGS. 5A and 5B illustrate a cross sectional view of a container 2 comprising a leg L at height Va according to FIG. 4A and height Vb according to FIG. 4B. At height Va the leg L has a cross sectional area A". At height Vb the leg L has a cross sectional area A'''. The annular space A in FIGS. 5A and 5B is equal to the cross-sectional area $A_{cs}$. Comparing of FIGS. 5A and 5B shows that the cross sectional area A" of the leg L is larger than the cross sectional area A''' of the leg L.

The process for the determination of the cross-sectional area is described on the basis of FIGS. 3, 4A and 4B. FIG. 3 shows the starting point of the measurement where the flowable medium 12 has height H' and the tap 8 is closed. The tap 8 is opened and the flowable medium 12 descends to a height H" as shown in FIG. 4A or a height H''' as shown in FIG. 4B. During the outflow of the flowable medium 12 at least one of the measuring means 7, 9, 10 or 11 is used to determine the height of the flowable medium. The heights H', H" and H''' can be used to calculate the volume of the leg between H' and H", H' and H''' or H" and H'''. It is also possible to calculate the cross-sectional area at height H', H" or H''' by using equation 10 as described here above.

In practice, the height differences between the individual measuring points will be smaller than in the above explanation. Thereby the measurement can become a nearly continuous measurement of the cross sectional area of the object.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

Example

A cylindrical container 2 (diameter 30 cm) provided with a tap 8 and only a pressure sensor 9 according to FIG. 1 was used. During the experiments the temperature of the water remained at a constant value.

Figure 7:
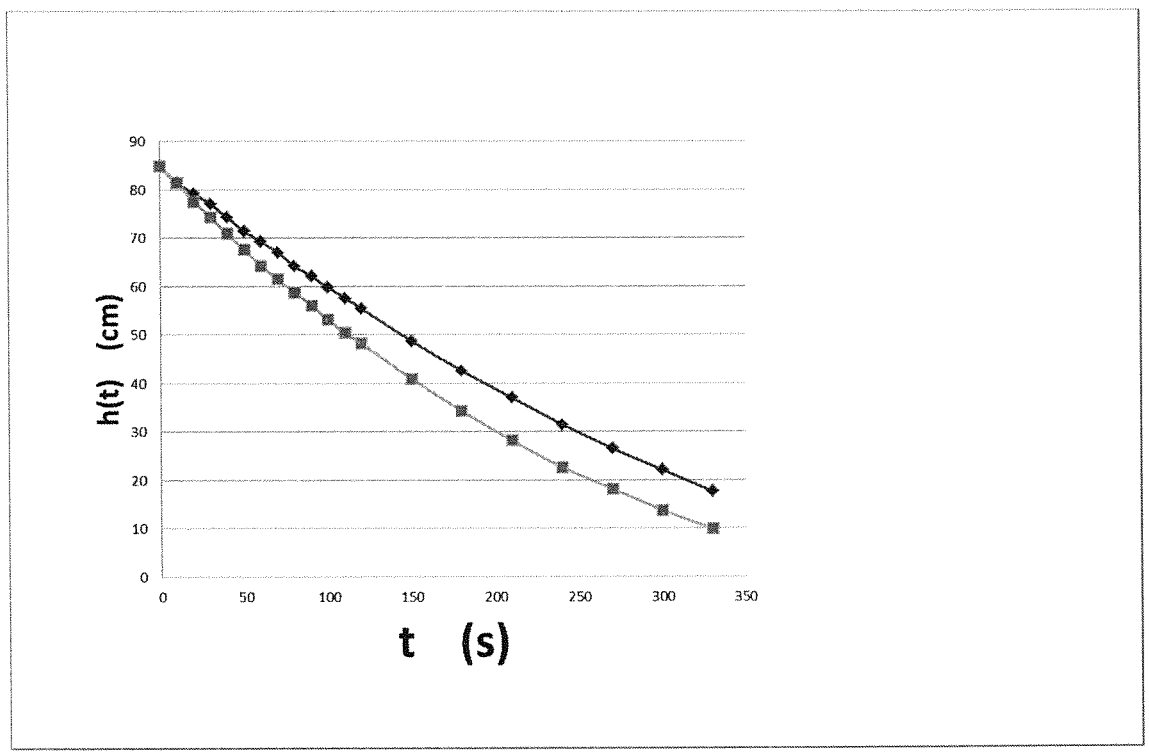
FIG. 7 is a representation of the height of a water column in a deflating cylindrical container. The lower curve in FIG. 7 represents the results of a container containing a leg of a shop-window dummy. The upper curve in FIG. 7 represents the reference wherein the container contained no object.

Time was monitored using a conventional watch and the water height was monitored by eye. Deflation of the container was done with only water in the container (reference) and subsequently with a leg of a shop-window dummy in the water in the container. The foot of the leg was placed on the bottom of the container and the leg touched the wall of the container at the top. The results of the test are presented by the lower curve in FIG. 7. The upper curve in FIG. 7 represents the reference.

The curves show that the rate of deflation $$\left(\frac{\Delta h}{\Delta t}\right)$$

is higher in the presence of the leg. The curve representing the situation where the leg is present shows a slope that is steeper at any height h(t), compared to the curve of the reference container without the leg.

The set of measuring points was mathematically processed as described above, rendering $$\left(\frac{\Delta h}{\Delta t}\right).$$

Thereafter, the cross-sectional area of the leg at any height was calculated starting from equation (10). For a cylindrical container $A_c = \pi R^2$ and the annular space is described by $\pi \cdot (R^2 - R_{leg}^2)$, assuming the leg is perfectly cylindrical at any height. This rendered the following equation:

$$\pi \cdot (R^2 - R_{leg}^2) * \frac{\Delta h}{\Delta t} = -C_c C_f \cdot \pi r^2 \cdot \sqrt{2 \cdot g \cdot h}$$

As $$\left(\frac{\Delta h}{\Delta t}\right),$$

at any height h was known, as well as R and r, the radius of the leg at any height could be calculated.

Figure 8:
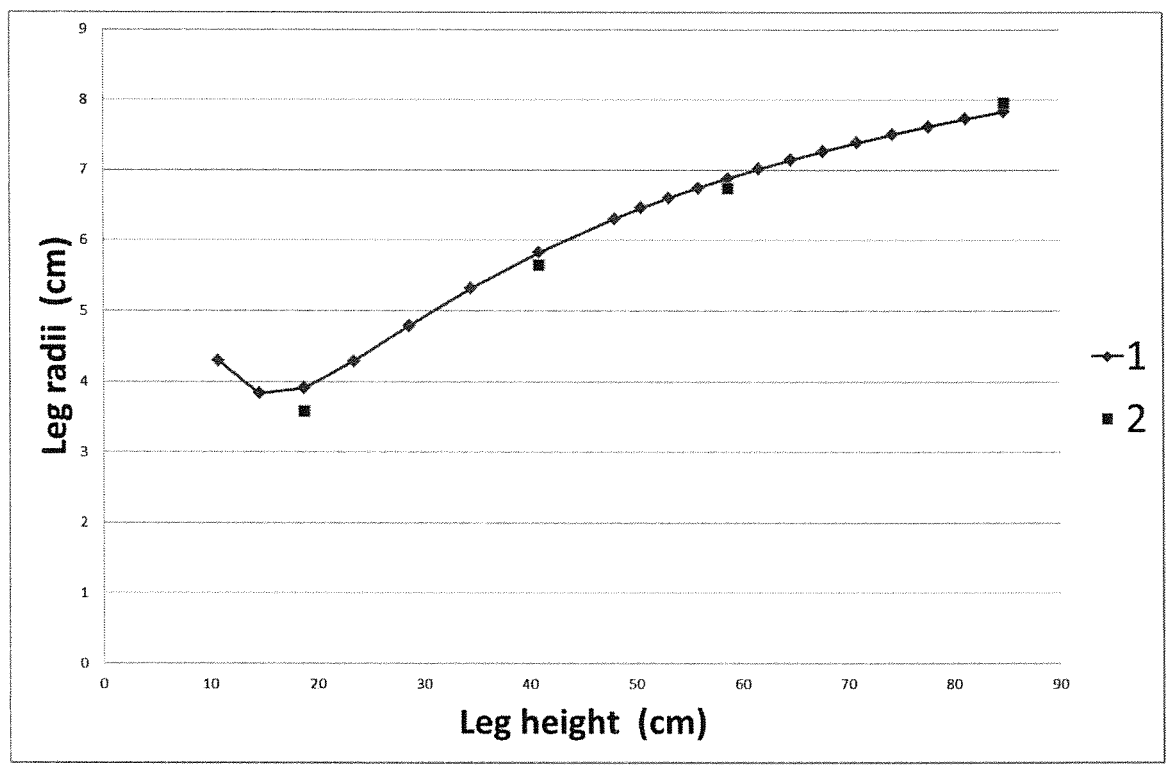
FIG. 8 represents a graph of the radius of the leg versus the height of the leg (1) This graph was compared with some measurements using a tailor tape (2).

In FIG. 8 this calculation of the radius of the leg was compared with some measurements using a tailor tape.

What is claimed is:

1. A process for the determination of a cross-sectional area ($A_O$) and volume of a part of a human body for assessing tissue edema using a device comprising a container that can hold a flowable medium, comprising the steps of:
    a. obtaining the device for the determination of the cross-sectional area ($A_O$) as a function of a height of the part of the human body, the device comprising, the container, wherein the container has a closed bottom, an open top, a side wall, a tap at a reference height,
    b. providing the flowable medium having a surface in the container,
    c. providing at least one measuring means for measuring a height of the surface of the flowable medium in the container relative to the reference height,
    d. determining the rate of deflation of the flowable medium in the container as a function of the height of the flowable medium to obtain a reference curve of the container, e. positioning the part of the human body having a vertical Z-axis relative to a (X,Y) plane of the bottom surface of the container such that the part of the human body is at least partly submerged in the flowable medium in the container, f. providing calculating means for determining the cross-sectional area in the (X,Y) plane relative to a position on the Z-axis and the volume of the part of the human body, g. opening the tap of the container to allow the flowable medium to flow out of the container, or removing the flowable medium by using a pump, or adding the flowable medium to the container, h. determining the height of the surface of the flowable medium relative to the reference height as a function of time (h(t)) during the outflow or inflow of the flowable medium from the container, i. determining the cross-sectional area ($A_O$) of the part of the human body as a function of the height relative to the reference height based on the determined height of the surface of the reference curve of the container as a function of time (h(t)) during the outflow or inflow of the flowable medium from the container in step g; and j. determining a volume of a defined segment of the part of the human body based on the cross-sectional area ($A_O$) as a function of the height, and k. assessing edema based on the determined volume of the defined segment of the part of the human body.

2. The process according to claim 1, further including the steps of adjusting the cross-sectional area ($A_O$) of the part of the human body as a function of height for an offset of the part of the human body relative to the reference height in a vertical direction of the part of the human body.

3. The process according to claim 1, wherein the container is cylindrical.

4. The process according to claim 3, wherein the determination of a cross-sectional area is performed according to an equation, wherein the equation is $$A_{cs} * \frac{\Delta h}{\Delta t} = -C_c C_f \cdot \pi r^2 \sqrt{2 \cdot g \cdot h(t)}$$

wherein
$A_{cs}$=cross-sectional area of the annular space between the part of the human body and the wall of the container $\frac{\Delta h}{\Delta t}$ = difference quotient, change in height of the flowable medium in the container as function of time r=radius of the tap opening,
$C_c$=factor correcting for contraction side effects,
$C_f$=factor correcting for friction side effects,
g=acceleration due to gravity
h(t)=height of the flowable medium as function of time and
t=time.

5. The process according to claim 1, wherein the flowable medium is a liquid.

6. The process according to claim 5, wherein the liquid is water.

7. The process according to claim 1, wherein the container is cylindrical and comprises one tap, the means for measuring the height is a pressure sensor and the flowable medium is water.

8. The process according to claim 7, wherein the determination of a cross-sectional area is performed according to an equation, wherein the equation is $$A_{cs} * \frac{\Delta h}{\Delta t} = -C_c C_f \cdot \pi r^2 \sqrt{2 \cdot g \cdot h(t)}$$

wherein
$A_{cs}$=cross-sectional area of the annular space between the part of the human body and the wall of the container $\frac{\Delta h}{\Delta t}$ = difference quotient, change in height of the flowable medium in the container as function of time r=radius of the tap opening,
$C_c$=factor correcting for contraction side effects,
$C_f$=factor correcting for friction side effects,
g=acceleration due to gravity
h(t)=height of the flowable medium as function of time and
t=time.

9. The process according to claim 1, wherein the determination of the cross-sectional area of the part of the human body in step i is performed according to a non-stationary mass balance equation and the Bernoulli equation.

10. The process according to claim 1, wherein the tissue edema in an arm or a leg is assessed.

11. The process of claim 1, wherein the part of the human body is an arm or leg.

12. The process according to claim 1, further including the step of adjusting the cross-sectional area ($A_O$) of the part of the human body as a function of height for an offset of the part of the human body relative to the reference height in a vertical direction of the part of the human body.

* * * * *